(12) United States Patent
Kikuchi

(10) Patent No.: US 10,786,197 B2
(45) Date of Patent: Sep. 29, 2020

(54) EVALUATION METHOD FOR SITE OF COLOR IRREGULARITY AND COLOR IRREGULARITY SITE EVALUATION APPARATUS

(71) Applicant: SHISEIDO COMPANY, LTD., Tokyo (JP)

(72) Inventor: Kumiko Kikuchi, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 151 days.

(21) Appl. No.: 16/090,666

(22) PCT Filed: Feb. 22, 2017

(86) PCT No.: PCT/JP2017/006522
§ 371 (c)(1),
(2) Date: Oct. 2, 2018

(87) PCT Pub. No.: WO2017/179304
PCT Pub. Date: Oct. 19, 2017

(65) Prior Publication Data
US 2019/0117147 A1 Apr. 25, 2019

(30) Foreign Application Priority Data

Apr. 15, 2016 (JP) ................ 2016-082380

(51) Int. Cl.
*G06K 9/62* (2006.01)
*A61B 5/00* (2006.01)
(Continued)

(52) U.S. Cl.
CPC ............ *A61B 5/444* (2013.01); *A61B 5/00* (2013.01); *A61B 5/107* (2013.01); *A61B 5/1032* (2013.01);
(Continued)

(58) Field of Classification Search
CPC ..... A61B 2576/00; A61B 5/443; A61B 5/444; A61B 5/1032; A61B 5/00; A61B 5/107;
(Continued)

(56) References Cited

U.S. PATENT DOCUMENTS 6,624,860 B1 * 9/2003 Narutaki ................ G02B 5/201
349/106
9,801,312 B2 10/2017 Kondo
(Continued)

FOREIGN PATENT DOCUMENTS

JP 2001-325584 11/2001
JP 2003-144393 5/2003
(Continued)

OTHER PUBLICATIONS

International Search Report for PCT/JP2017/006522 dated May 16, 2017.
(Continued)

*Primary Examiner* — Ali Bayat
(74) *Attorney, Agent, or Firm* — IPUSA, PLLC

(57) ABSTRACT

An evaluation method of evaluating a color irregularity site (a blemish) includes a color irregularity site detection step (step S102) of detecting a plurality of color irregularity sites respectively from a first skin image and a second skin image different from the first skin image, a gravity center position calculation step (step S108) of calculating gravity center positional coordinates of the color irregularity sites respectively for the first skin image and the second skin image, and a matching process step (step S110) of matching the plurality of color irregularity sites included in the first skin image with the plurality of color irregularity sites included in the second skin image based on the calculated gravity center positional coordinates of the color irregularity sites.

11 Claims, 14 Drawing Sheets

(51) Int. Cl.
*A61B 5/107* (2006.01)
*G06T 7/66* (2017.01)
*G06T 7/33* (2017.01)
*G06T 7/90* (2017.01)
*A61B 5/103* (2006.01)
*G06K 9/46* (2006.01)

(52) U.S. Cl.
CPC ............ *A61B 5/443* (2013.01); *G06K 9/4652* (2013.01); *G06K 9/6212* (2013.01); *G06T 7/337* (2017.01); *G06T 7/66* (2017.01); *G06T 7/90* (2017.01); *A61B 2576/00* (2013.01); *G06T 2207/10024* (2013.01); *G06T 2207/30088* (2013.01)

(58) Field of Classification Search
CPC .. G06T 7/337; G06T 7/90; G06T 7/66; G06T 2207/10024; G06T 2207/30088; G06K 9/4652; G06K 9/6212
USPC .......................................................... 382/165
See application file for complete search history.

(56) References Cited

U.S. PATENT DOCUMENTS

| | | | | |
|---|---|---|---|---|
| 2006/0250607 | A1* | 11/2006 | Takahashi | G03F 7/706 356/124 |
| 2007/0002342 | A1* | 1/2007 | Morales | H04N 1/6055 358/1.9 |
| 2007/0291311 | A1* | 12/2007 | Yano | H04N 1/6088 358/2.1 |
| 2009/0304243 | A1 | 12/2009 | Mertz et al. | |
| 2009/0327890 | A1 | 12/2009 | Mertz et al. | |
| 2011/0040192 | A1 | 2/2011 | Brenner et al. | |
| 2012/0092740 | A1* | 4/2012 | Kimura | G02B 26/127 359/204.1 |
| 2012/0114202 | A1 | 5/2012 | Manson | |
| 2013/0188878 | A1 | 7/2013 | Kacenjar | |
| 2014/0043599 | A1* | 2/2014 | Takaie | G01J 9/00 356/121 |
| 2015/0213619 | A1 | 7/2015 | Nakamura et al. | |
| 2016/0106198 | A1* | 4/2016 | Yoshida | G01N 21/27 356/402 |
| 2016/0124221 | A1* | 5/2016 | Huang | G02B 27/0927 359/239 |
| 2019/0096093 | A1* | 3/2019 | Shinoda | A45D 44/005 |

FOREIGN PATENT DOCUMENTS

| | | |
|---|---|---|
| JP | 3727807 | 12/2005 |
| JP | 2012-211886 | 11/2012 |
| JP | 2013-090752 | 5/2013 |
| JP | 2014-234938 | 12/2014 |
| JP | 2015-198785 | 11/2015 |
| JP | 2015-205222 | 11/2015 |
| JP | 2016-096931 | 5/2016 |
| WO | 2014/172671 | 10/2014 |

OTHER PUBLICATIONS

Lisa Gottesfeld Brown: "A Survey of Image Registration Techniques", ACM Computing Surveys, NY, US, vol. 24, No. 4, Dec. 1, 1992, ISSN: 0360-0300, DOI: 10.1145/146370, 146374.
Extended European Search Report for 17782122.0 dated Sep. 30, 2019.

* cited by examiner

FIG.7
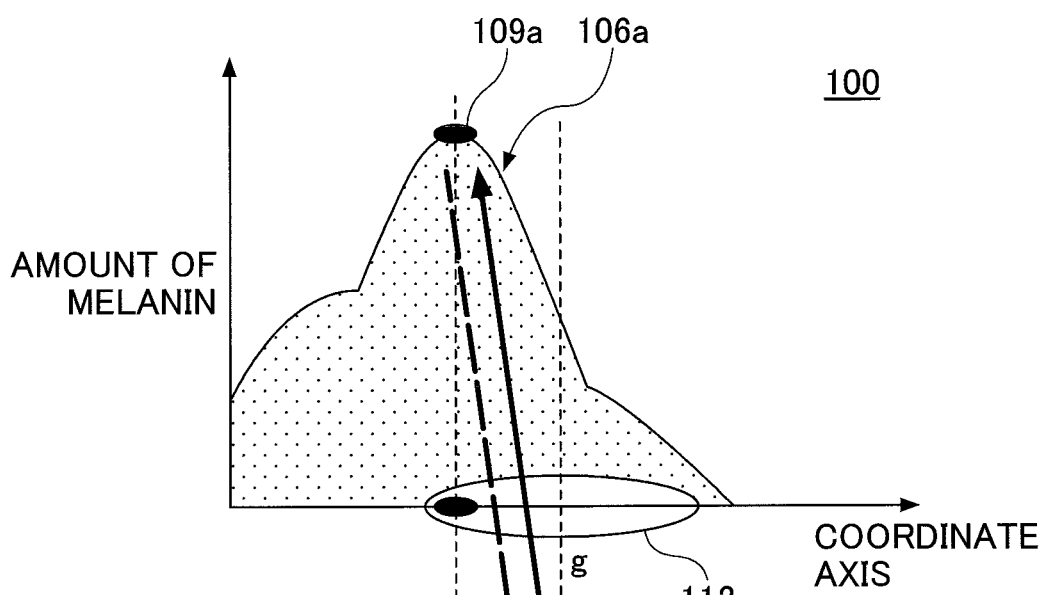
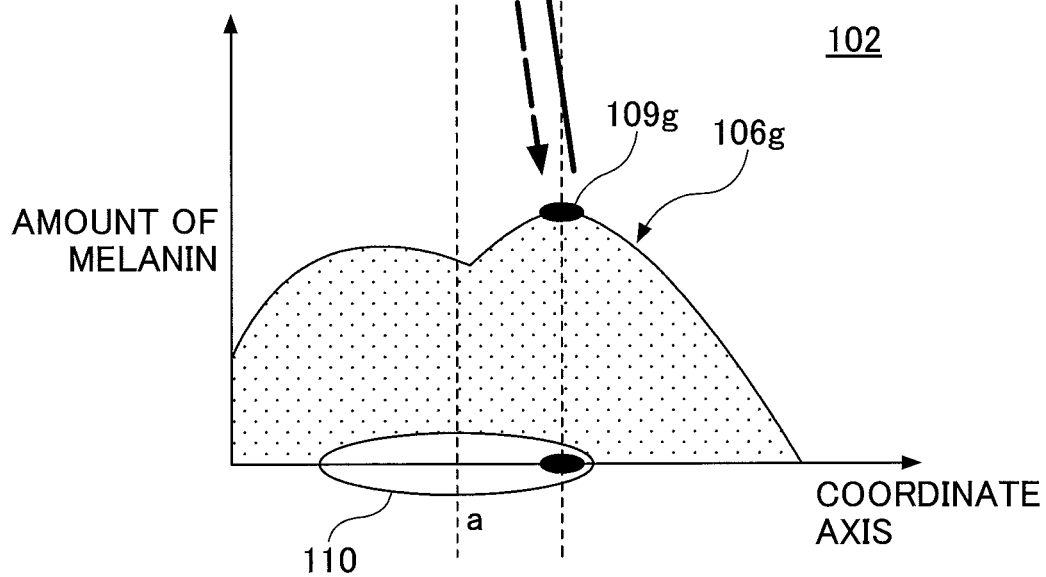

FIG.10A

| BLEMISH ID (100) | GRAVITY CENTER | PLANER DIMENSION | AMOUNT OF MELANIN | BLEMISH CLASSIFICATION |
|---|---|---|---|---|
| B001 | X1, Y1 | xx | xx | LARGE, PALE |
| B002 | X2, Y2 | xx | xx | SMALL, PALE |
| B003 | X3, Y3 | xx | xx | MIDDLE, DEEP |
| ... | ... | ... | ... | ... |

FIG.10B

| BLEMISH ID (102) | GRAVITY CENTER | PLANER DIMENSION | AMOUNT OF MELANIN | BLEMISH CLASSIFICATION |
|---|---|---|---|---|
| A001 | X21, Y21 | xx | xx | MIDDLE, PALE |
| A002 | X22, Y22 | xx | xx | SMALL, PALE |
| A003 | X23, Y23 | xx | xx | SMALL, DEEP |
| A004 | X24, Y24 | xx | xx | SMALL, PALE |
| ... | ... | ... | ... | ... |

FIG.10C

| BLEMISH ID (100) | BLEMISH ID (102) | CHANGE PATTERN | STATE CHANGE |
|---|---|---|---|
| B001 | A001, A002 | DIVISION | xx |
| B002 | — | DISAPPEAR-ANCE | xx |
| B003 | A003 | MAINTENANCE | REDUCTION OF PLANAR DIMENSION |
| — | A004 | GENERATION | xx |
| ... | ... | ... | ... |

EVALUATION METHOD FOR SITE OF COLOR IRREGULARITY AND COLOR IRREGULARITY SITE EVALUATION APPARATUS

TECHNICAL FIELD

The present invention relates to an evaluation method for a site of color irregularity and a color irregularity site evaluation apparatus.

BACKGROUND ART

For example, there is known a method of quantifying color information or pigment component information of a blemish or a freckle, which is specified from among a site around an eye, a site of cheek, or the like using eyesight, and the blemish and freckle are evaluated based on the quantified color information or pigment component information. The quantification of the color information is based on the mean value in a measurement area for the main component point related to melanin obtained by performing a main component analysis using, for example, spectral reflectance data of multiple wavelengths (for example, Patent Document 1).

PRIOR ART DOCUMENTS

Patent Documents

[Patent Document 1] Japanese Unexamined Patent Publication No. 2003-144393
[Patent Document 2] Japanese Unexamined Patent Publication No. 2001-325584

SUMMARY OF THE INVENTION

Problem to be Solved by the Invention

The state of a color irregularity site such as blemish may change with advancing age or an influence of seasons. Further, the state of a certain color irregularity site may change by the influence of a medical agent such as a skin-lightening agent. However, the conventional technique is not possible to identify each change in the color irregularity sites in evaluating the color irregularity sites.

Patent Document 2 discloses a method of registering at least two images. Disclosed is that specified structure focused-on images, on which a specified structure is focused, are acquired, a relationship of structural corresponding positions is acquired between the specified structure focused-on images, and the at least two images are registered based on the acquired relationship of structural corresponding positions. However, this method of registering the at least two images cannot cause the color irregularity sites of the at least two images to be associated.

According to a first aspect of the invention, changes in various color irregularity sites included in the skin image are captured and evaluated.

Means for Solving the Problem

According to an aspect, there is provided an evaluation method of evaluating a color irregularity site including a color irregularity site detection step of detecting a plurality of color irregularity sites respectively from a first skin image and a second skin image different from the first skin image, a gravity center position calculation step of calculating gravity center positional coordinates of the color irregularity sites respectively for the first skin image and the second skin image, and a matching process step of matching the plurality of color irregularity sites included in the first skin image with the plurality of color irregularity sites included in the second skin image based on the calculated gravity center positional coordinates of the color irregularity sites.

Effect of the Invention

A change in various color irregularity sites included in a skin image is captured and evaluated.

BRIEF DESCRIPTION OF THE DRAWINGS

FIG. 7 schematically illustrates matching between blemishes.
FIG. 10A illustrates an example of information related to each blemish.
FIG. 10B illustrates another example of the information related to each blemish.
FIG. 10C illustrates another example of the information related to each blemish.

MODE OF CARRYING OUT THE INVENTION

Hereinafter, a mode of carrying the present invention is described with reference to figures. The present invention is not limited to the specifically disclosed embodiments, and variations and modifications may be made without departing from the scope of the present invention.

Within the embodiment, described below is a case where a blemish is subject to an example of a color irregularity site, and a blemish evaluation process is exemplified as an evaluation method for evaluating a color irregularity site. Here, the blemish corresponds to a state where the border between a site on which a pigment such as a melanin pigment deposits on the bare skin and another site on which the pigment does not deposit is clearly distinguishable. Specifically, the blemish includes senile pigment freckle, solar lentigo, post-inflammatory pigmentation, freckle, chloasma, or the like, for example.

Figure 1:
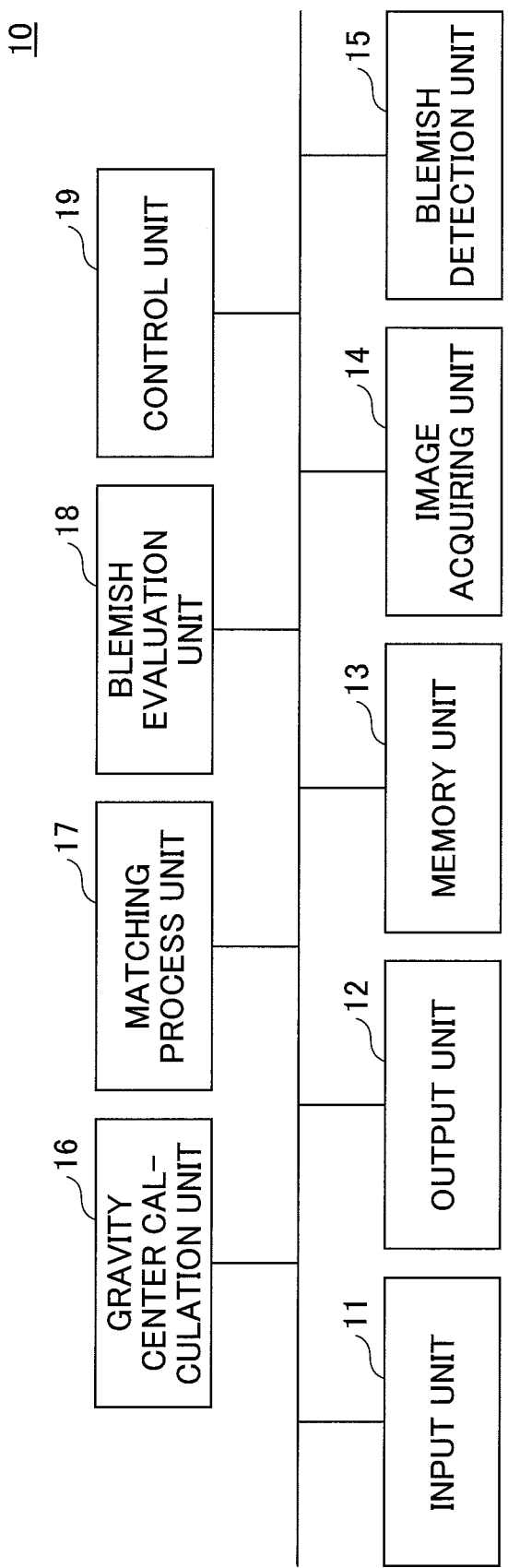
FIG. 1 illustrates an example of a functional configuration of a blemish evaluation apparatus.

FIG. 1 illustrates an example of a functional configuration of a blemish evaluation apparatus.

The blemish evaluation apparatus 10 includes an input unit 11, an output unit 12, a memory unit 13, an image acquiring unit 14, a blemish detection unit 15, a gravity center position calculation unit 16, a matching process unit 17, a blemish evaluation unit 18, and a control unit 19.

The input unit 11 receives inputs of starting, ending, and setting various instructions related to the blemish evaluation process from a user or the like who uses the blemish evaluation apparatus 10. The output unit 12 outputs a content input by the input unit 11 or a content performed based on the content input by the input unit 41. The output unit 12 performs a process of causing results obtained by the processes in, for example, the image acquiring unit 14, the blemish detection unit 15, the gravity center position calculation unit 16, the matching process unit 17, the blemish evaluation unit 18, or the like to be displayed on the display or the like.

Within the embodiment, the image acquiring unit 14 acquires a first skin image and a second skin image that differs from the first skin image. Here, the first skin image and the second skin image may be skin images obtained by capturing an identical subject portion of an identical test subject at different times.

Further, the first skin image and the second skin image may be a skin image by which an entire cheek of the test subject.

Further, the first skin image and the second skin image may be skin images from which a site (e.g., eye area, cheek, or the like) specified from a face image of a test subject captured by, for example, a skin image analyzer (SIA) system that includes a diffusion illumination box and a digital camera is extracted.

The blemish detection unit 15 detects multiple blemishes each of the first skin image and the second skin image. The gravity center position calculation unit 16 calculates gravity center positional coordinates respectively of the blemishes on the first skin image and the second skin image. The matching process unit 17 causes multiple blemishes included in the first skin image and multiple blemishes included in the second skin image to match based on the gravity center positional coordinates of the blemishes calculated by the gravity center position calculation unit 16.

The blemish evaluation unit 18 evaluates a change in the blemishes based on a relation of matching the blemishes matched by the matching process unit 17.

The control unit 19 controls the entire components of the blemish evaluation apparatus 10. The control unit 19 controls at least one of blemish detection, calculation of the position of the gravity center, the matching process, the blemish evaluation, and soon. However, the content controlled by the control unit 19 is not limited thereto.

The memory unit 13 stores various information necessary in this embodiment. Specifically, the memory unit 13 stores various programs, various setup information, and so on for executing the blemish evaluation process of the embodiment. The memory unit 13 stores the first and second images, information related to the blemishes included in the skin images (the number of the blemishes, the planar dimensions of the blemishes, the deepness of the blemishes, the gravity center positional coordinates of the blemishes, the relation of the blemishes, and so on), an evaluation result, and so on.

Here, the memory unit 13 stores an aggregate of various information and may have a function as a database that can be searched using, for example, a keyword and systematically structured so as to be extracted. Further, information stored in the memory unit 13 may be acquired from an external apparatus through a communication network represented by, for example, the Internet and a Local Area Network (LAN).

The blemish evaluation apparatus 10 can be implemented by installing an execution program (a blemish evaluation program) for causing various functions of the blemish evaluation apparatus 10 onto a general-purpose computer such as a personal computer (PC), a smartphone, a tablet terminal, and so on.

(Hardware Structure)

Figure 2:
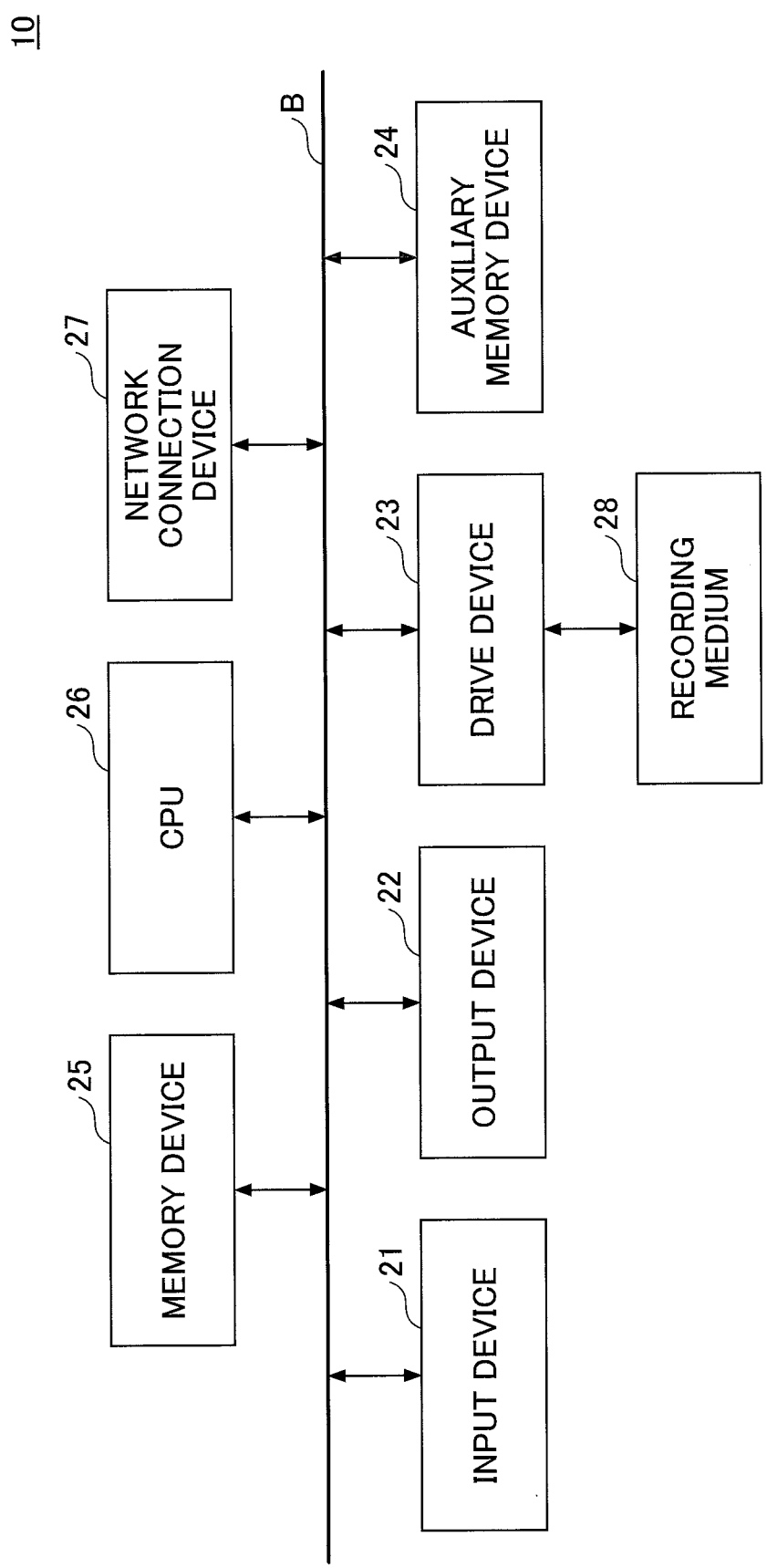
FIG. 2 illustrates an example hardware structure enabling the blemish evaluation process of the embodiment of the present invention.

FIG. 2 illustrates an example of a hardware structure enabling the blemish evaluation process. The blemish evaluation apparatus 10 includes an input device 21, an output device 22, a drive device 23, an auxiliary storage device 24, a memory device 25, a Central Processing Unit (CPU) 26 for performing various controls, and a network connection device 27. These are mutually connected via a system bus B.

The input device 21 is a keyboard operated by a user or the like or a pointing device such as a mouse. Further, the input device 21 may be a voice input device 21 such as a mike, to which an input is possible by voice, for example.

The output device 22 may be a display or a speaker. Further, the output device 22 may be a print device such as a printer.

For example, in a case where the blemish evaluation apparatus 10 is a smartphone, a tablet, or the like, the above input device 21 and the above output device 22 may have a structure of input-output integration type such as a touch panel.

In the embodiment of the present invention, the execution program installed on the computer may be provided by a portable recording medium 28 such as a Universal Serial Bus (USB) and a CD-ROM. The recording medium 28 having the execution program recorded on it may be mounted on the drive device 23. The execution program included in the recording medium 28 is installed on the auxiliary storage device 24 via the drive device 23 from the drive device 23.

The auxiliary storage device 24 is a storage means such as a hard disk. The auxiliary storage device 24 can store the execution program of the embodiment of the present invention, and the control program installed on the computer, and so on, thereby enabling to input or output these when necessary.

The memory device 25 stores the execution program which is read out of the auxiliary storage device 24 by the CPU 26, and so on. The memory device 25 includes a Read Only Memory (ROM), a Random Access Memory (RAM), or the like. The above auxiliary storage device 24 and the memory device 25 may be integrally structured as a single device for storing information.

The CPU 26 controls entire processes of the computer such as various calculations and inputs and outputs of data to and from various portions in a hardware configuration in order to perform the blemish evaluation process based on the control program such as an operating system (OS) and the execution program stored in the memory device 25. The various information or the like necessary for running the program may be obtained from the auxiliary storage device 24. The results of the execution may be stored in the auxiliary storage device 24.

The network connection device 27 is connected with a communication network represented by the Internet, LAN, or the like so as to acquire the execution program and the various data from another device or the like connected to the communication network. Further, the network connection device 27 can provide an execution result acquired by executing the program to another device.

With the above hardware structure, the blemish evaluation process of the embodiment can be executed. Further, the blemish evaluation process can be easily performed using a general-purpose personal computer (PC) by installing the execution program.

(Blemish Evaluation Process)

Figure 3:
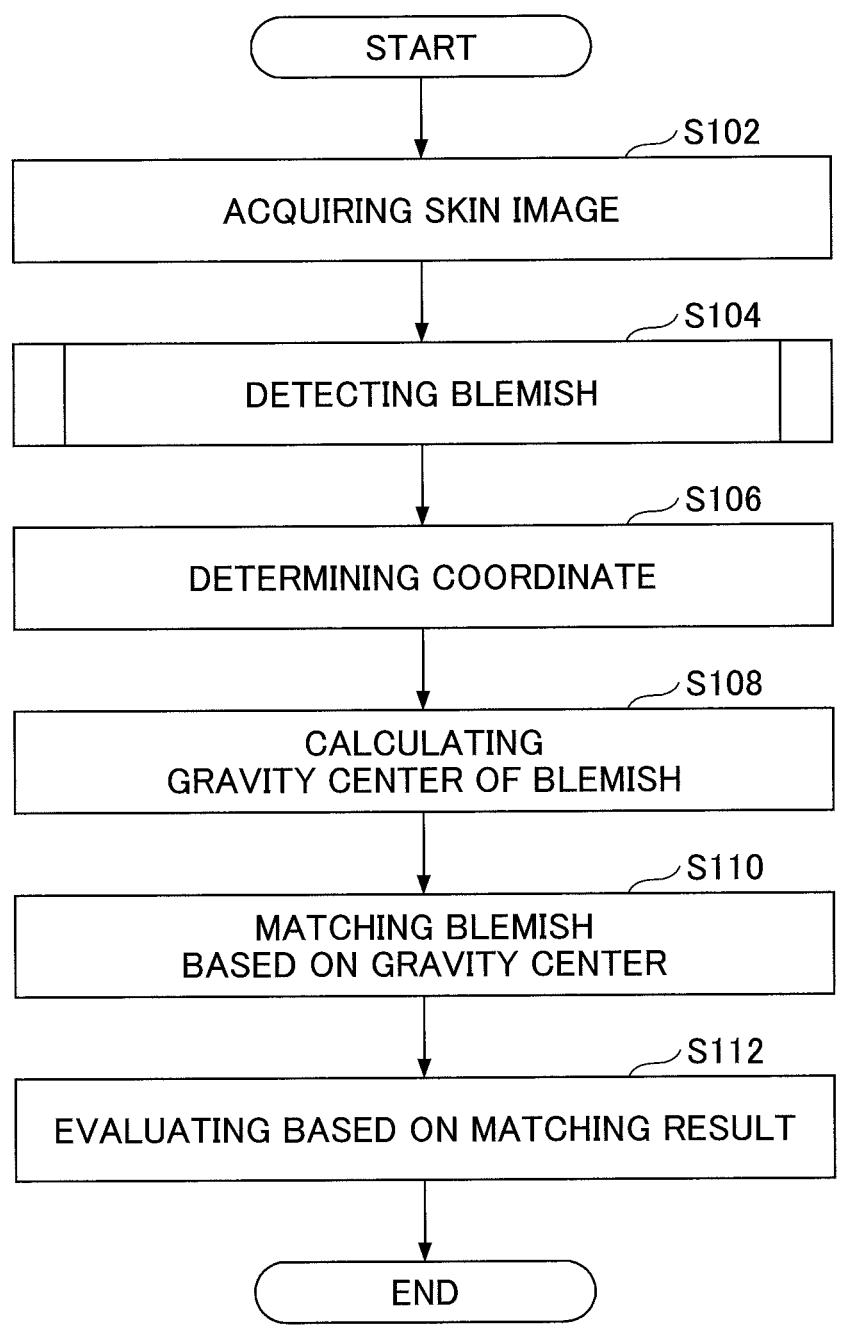
FIG. 3 is a flowchart illustrating an example of the blemish evaluation process.

FIG. 3 is a flowchart illustrating an example of the blemish evaluation process.

Within the embodiment, the image acquiring unit 14 acquires two skin images, namely the first skin image and the second skin image (Step S102). For example, the first skin image and the second skin image are images of an identical test subject at different times such as images before applying and a predetermined time period after applying a medical agent such as a skin-whitening medical agent to the identical test subject, images of the identical test subject changed along with aging, and images of the identical test subject in different seasons. In the embodiment described below, the second skin image is a skin image obtained by capturing the identical subject portion of the identical subject in the first skin image after the first skin image has been captured.

The image acquiring unit 14 can acquire a skin image (pixel area of 500×500 pixels), on which a predetermined area of a cheek of the test subject are captured as the first and second skin images, so as to be an analyzation area. Further, the image acquiring unit 14 may extract the predetermined area (pixel area of 500×500 pixels) of the cheek as the analyzation area based on a facial image contour acquired as the facial image of the test subject so as to obtain the first and second skin images. However, even in a case where a shift occurs in aligning the first skin image and the second skin image in the later process of step S106, in order to ensure a sufficient analyzation area, the first and second skin images 100 and 102 may include an area wider that the above analyzation area.

Figure 4:
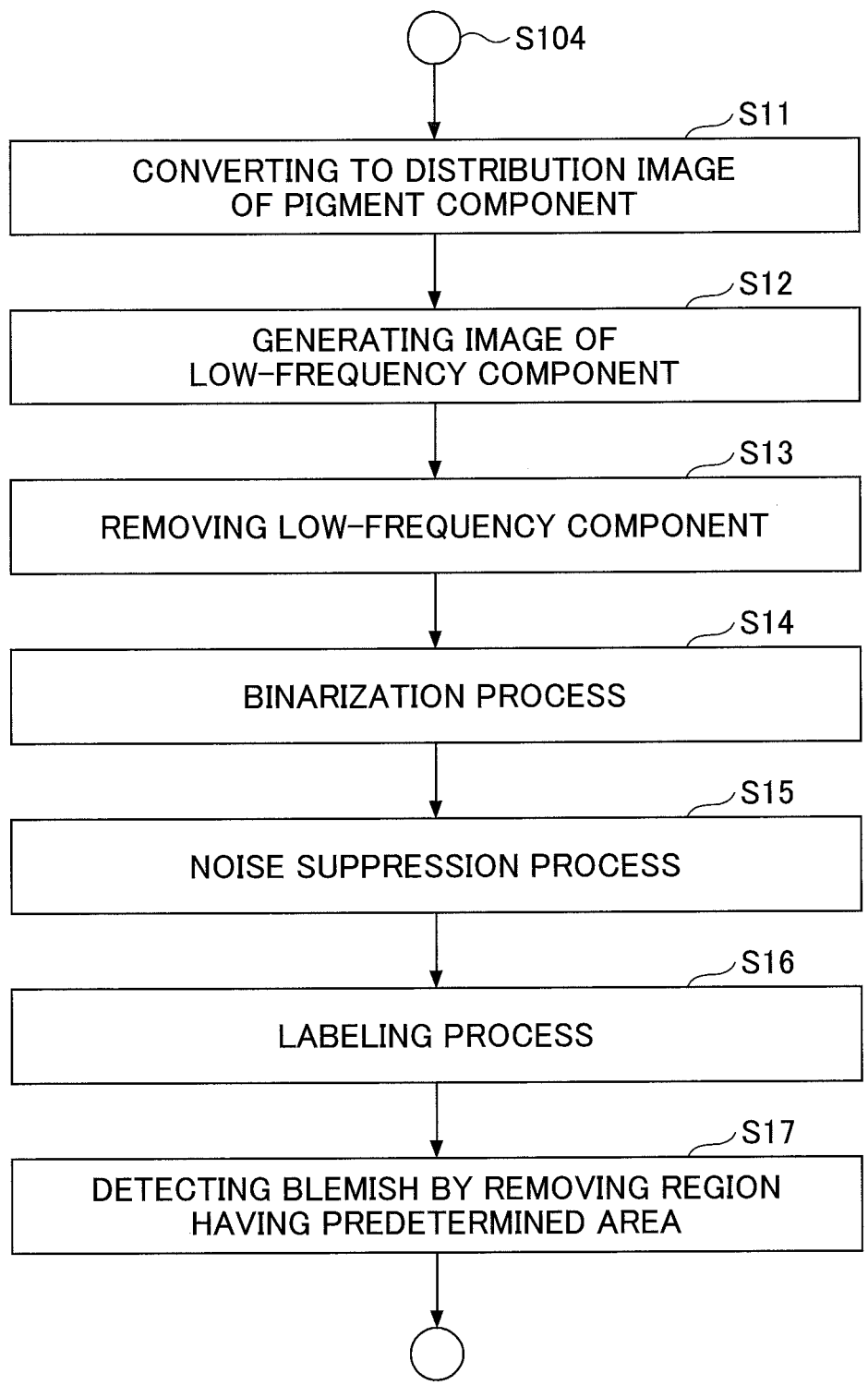
FIG. 4 is a flowchart illustrating an example of the blemish evaluation process.

The blemish detection unit 15 performs imaging process for the first skin image and the second skin image acquired by the image acquiring unit 14 and detects a blemish from each of the first skin image and the second skin image (step S104). Referring to FIG. 4, detailed processes by the blemish detection unit 15 are described.

(Blemish Detection Process)

FIG. 4 is a flowchart representing the blemish detection process of step S104 in detail. The following processes are performed for each of the first skin image and the second skin image.

The blemish detection unit 15 calculates pigment compositions such as a melanin component and a hemoglobin component in a skin image as the analyzation area and converts to an image (a distribution image of the pigment compositions) illustrating the deepness of the pigment compositions and their distribution state (step S11). Specifically, the blemish detection unit 15 acquires an RGB value of the RGB colorimetric system, a CIE-XYZ value as a CIE international standard value obtained by converting from the RGB colorimetric system, a color data Lab value, or the like.

The RGB value of the RGB colorimetric system can be converted to the CIE-XYZ value using the following formula.

$$X = 0.001645 \times R + 0.001116 \times G + 0.000314 \times B + 2.585143$$

$$Y = 0.001110 \times R + 0.002080 \times G + 0.000065 \times B + 2.359088$$

$$Z = 0.000439 \times R + 0.000610 \times G + 0.002439 \times B + 2.757769 \quad \text{[Formula 1]}$$

The XYZ values obtained from Formula 1 can be converted to a pigment composition such as a melanin component and a hemoglobin component using the following Formula 2 using a measure described in Japanese Patent Number 3727807 granted in the name of the applicant of the present application.

$$\text{Amount of Melanin} = -4.861 \times \log 10(1/X) + 1.268 \times \log 10(1/Y) + 4.669 \times \log 10(1/Z) + 0.063$$

$$\text{Amount of hemoglobin} = -32.218 \times \log 10(1/X) + 37.499 \times \log 10(1/Y) - 4.495 \times \log 10(1/Z) + 0.444 \quad \text{[Formula 2]}$$

Next, the blemish detection unit 15 removes a low frequency component from the distribution image of the pigment composition obtained in step S11. With this, it is possible to remove an influence of large undulation corresponding to a shadow caused by a shape of face, for example. The blemish detection unit 15 removes a band of about 40.0 mm as the half maximum full-width or greater in order to cancel the influence of shadow. Specifically, the blemish detection unit 15 generates an image of the low frequency component using a bandpass filter of Gaussian functions (Step S12). Subsequently, the blemish detection unit 15 subtracts the image of the low frequency component obtained in step S12 from the distribution image of the pigment composition obtained in the process of step S11 (Step S13).

Next, the blemish detection unit 15 performs a binarization process for the image obtained in step S13 (Step S14). The binarization process, determines an pixel having a melanin value (a high melanin value) greater than a threshold value that is, for example, the mean value of +0.01 to +0.30 as the deepness of the melanin component. With this, a normal skin part and a high melanin part are distinguished.

Next, the blemish detection unit 15 performs a noise suppression process for the image obtained in step S14 (Step S15). The noise suppression process can be performed by using, for example, a median filter (5×5 pixels). However, the embodiment is not limited thereto.

Next, the blemish detection unit 15 performs a labeling process of labelling an area where the pixels having the high melanin values are continuously arranged within the image obtained by step S15 as a single pigment deposition site (Step S16). The blemish detection unit 15 couples parts at which pixels identified as the pixel of the high melanin values are adjacent and extracts the coupled pixel group as the single pigment deposition site.

Next, the blemish detection unit 15 detects the pigment deposition site that remains after removing a planar dimension (e.g., an actual size of 1.0 mm$^2$) equal to or less than a predetermined area from among the pigment deposition site labeled in step S16, as the blemish (Step S17). With this, a small extracted matter such as a pore is removed to accurately detect the blemish.

The above process of the blemish detection unit 15 is described in the Japanese Patent Application Number 2014-234938, and the contents of the Japanese Patent Application Number 2014-234938 can be appropriately used for the above process.

Referring back to FIG. 3, the gravity center position calculation unit 16 aligns the positions of the first skin image and the second skin image based on multiple blemishes detected from the first skin image and multiple blemishes detected from the second skin image to determine a reference point of the coordinate (Step S106). Here, the position alignment can be conducted using pattern recognition based on distributions of the blemishes respectively detected from the first skin image and the second skin image.

Figure 5A:
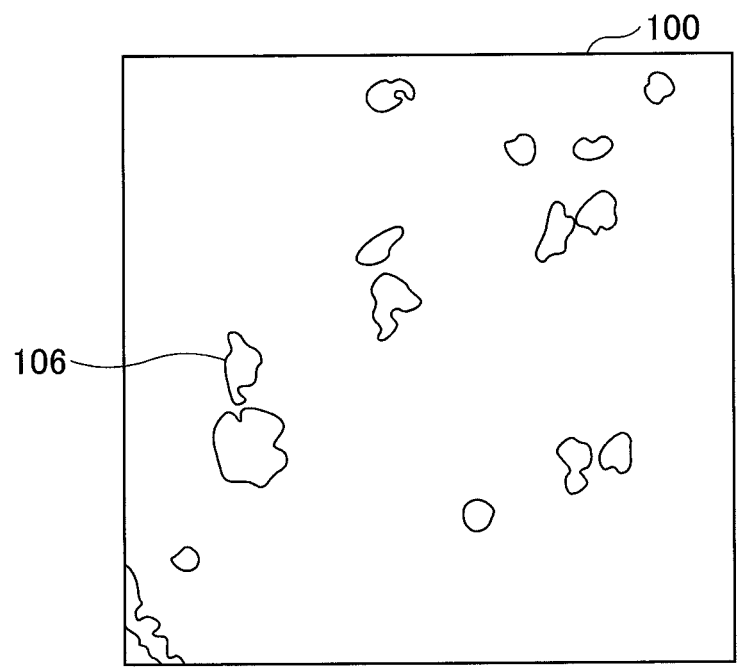
FIG. 5A schematically illustrates an example of a process of registering a first skin image and a second skin image and determining a reference point of a coordinate.
Figure 5B:
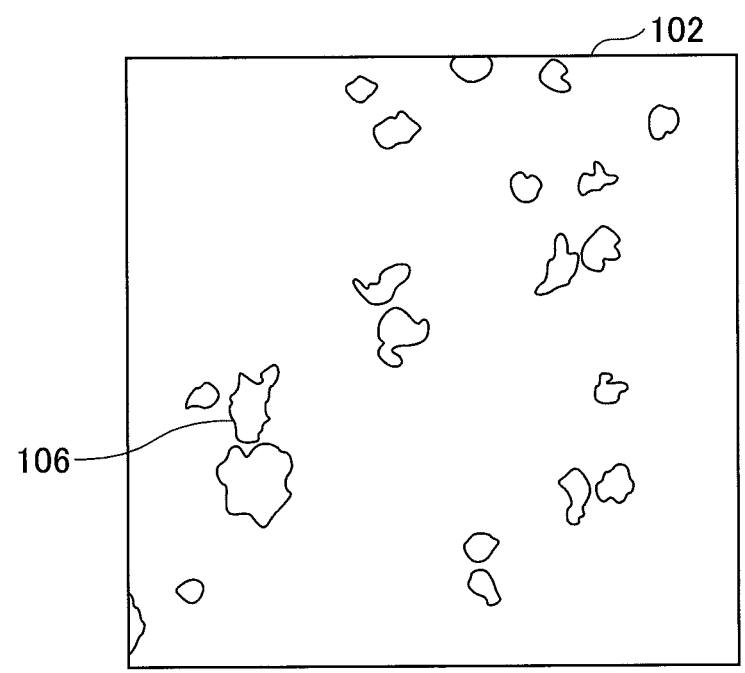
FIG. 5B schematically illustrates the example of the process of registering the first skin image and the second skin image and determining the reference point of the coordinate.
Figure 5C:
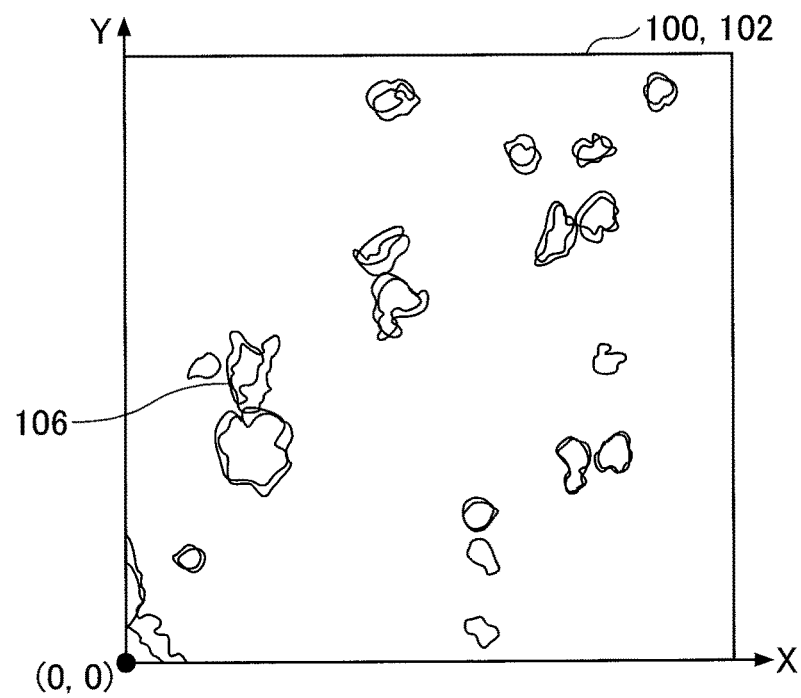
FIG. 5C schematically illustrates the example of the process of registering the first skin image and the second skin image and determining the reference point of the coordinate.

FIGS. 5A to 5C schematically illustrate an example of this process. FIG. 5A illustrates the first skin image 100, and FIG. 5B illustrates the second skin image 102. In FIG. 5C, the positions of the first skin image 100 and the second skin image 102 are aligned. The gravity center position calculation unit 16 aligns the positions of the first skin image 100 and the second skin image 102 based on distribution of the multiple blemishes included in the first skin image 100 and the second skin image 102 to align the coordinates of the first skin image 100 and the second skin image 102. For example, a predetermined lower left position is determined to be the reference point of the XY coordinate system. With this, in a latter process, the blemish 106 included in the first skin image 100 and the blemish included in the second skin image 102 are accurately matched.

Referring back to FIG. 3, the gravity center position calculation unit 16 calculates the gravity center positional coordinates of the blemishes 106 of the first skin image 100 and the second skin image 102 with respect to the reference point determined in step S106 (Step S108).

Figure 6:
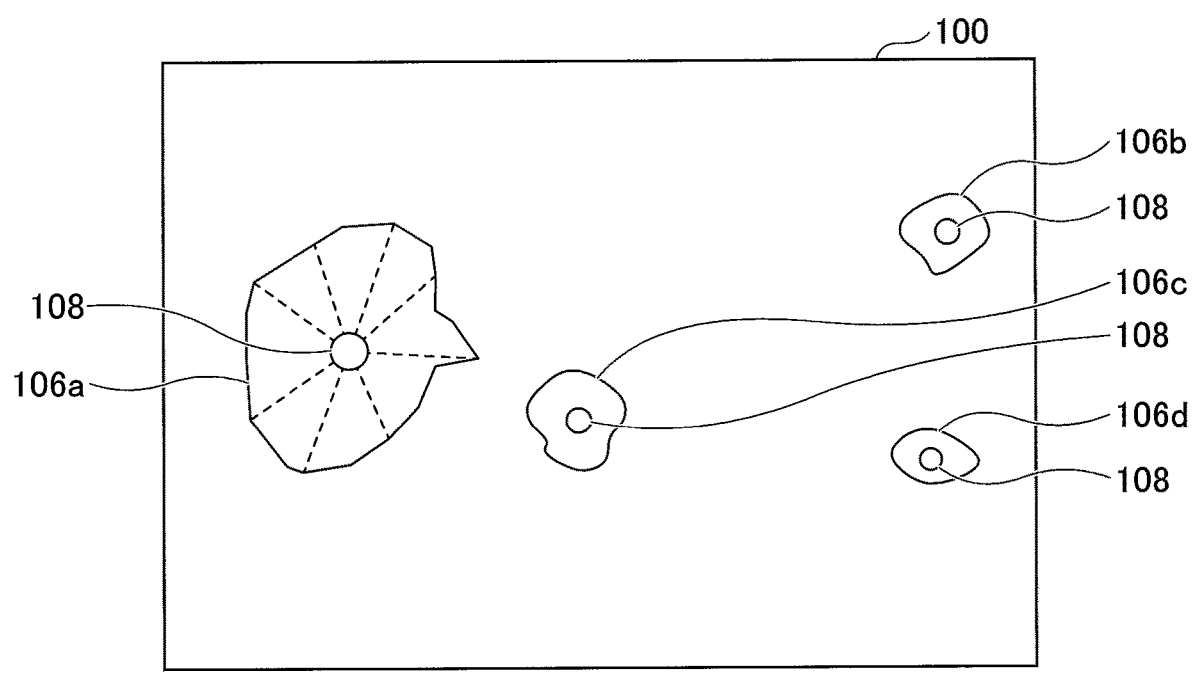
FIG. 6 schematically illustrates an example of a process of calculating gravity center positional coordinates of the various blemishes.

FIG. 6 schematically illustrates an example of this process. The gravity center position calculation unit 16 calculates the positional coordinates of the gravity centers 108 of the blemishes on the first skin image 100 and the second skin image 102.

The positional coordinate of the gravity center 108 can be calculated from the positional coordinates of all pixels forming the blemish areas, for example. Specifically, the positional coordinate of the gravity center 108 can be obtained by calculating averages of the X coordinates and the Y coordinates of all pixels that form the blemish area.

Further, as another example, the positional coordinate of the gravity center 108 may be calculated using the following procedure.

(1) A Method of Calculating from all Pixels Forming the Contour of Each Blemish

Provided that the number of all pixels forming the contours of the blemishes is n, the X coordinate of the gravity center 108 can be obtained by adding the X coordinates of all points and dividing the added X coordinates by n. The Y coordinate of the gravity center 108 is calculated in a manner similar thereto.

(2) A Method of Weighting Melanin Deepness on all Pixels Forming all Pixels Forming the Blemish Areas After weighting all the pixels forming the blemish area using the melanin deepness (multiplication for the coordinate), the average of the X coordinate values and the average of the Y coordinate values are calculated as the method (2).

(3) A Method of Performing Ellipse Fitting to Acquire the Center of the Ellipse

The above methods are an example, and the other method can be appropriately selected.

Referring back to FIG. 3, the matching process unit 17 performs matching between the blemishes 106 based on the gravity center positional coordinates of the blemishes of the first skin image 100 and the second skin image 102 (Steps S110). The matching process unit 17 performs a first searching step of detecting the blemish 106 corresponding to each blemish 106 on the first skin image 100 from the second skin image 102, and a second searching step of detecting the blemish 106 corresponding to each blemish 106 on the second skin image 102 from the first skin image 100.

FIG. 7 schematically illustrates an example of this process. FIG. 7 schematically illustrates an example of a relation between the coordinate axis of the skin images and the amount of melanin. In FIG. 7, (a) corresponds to the first skin image 100, and (b) corresponds to the second skin image 102.

At first, the first searching step is described. The matching process unit 17 searches the second skin image 102 for the blemish 106a of the first skin image 100 within a predetermined range around the subject coordinate ("a" in (b) of FIG. 7) of the second skin image 102 corresponding to the gravity center positional coordinate 109a of the blemish 106a.

Here, it is assumed that the gravity center positional coordinate 109g of the blemish 106g approaches closest to the subject coordinate a from among the blemishes whose gravity center positional coordinates exist inside the search range 110 of the second skin image 102. In this case, the matching process unit 17 matches the blemish 106g whose gravity center positional coordinate 109g is closest to the subject coordinate a from among the blemishes having the gravity center positional coordinates inside the search range 110 of the second skin image 102 with the blemish 106a of the first skin image 100 (matching indicated by an arrow of broken line). The matching process unit 17 performs this process for each blemish on the first skin image 100.

Further, in a case where the blemish whose gravity center positional coordinate existing inside the search area of the second skin image 102, the matching process unit 17 causes an issue that the blemish corresponding to the blemish of the first skin image 100 is not present on the second skin image 102 to be associated with the blemish of the first skin image 100.

Next, the second searching step is described. The matching process unit 17 searches the first skin image 100 for the blemish 106g of the second skin image 102 within a predetermined range around the subject coordinate ("g" in (a) of FIG. 7) of the first skin image 100 corresponding to the gravity center positional coordinate 109g of the blemish 106g.

Here, it is assumed that the gravity center positional coordinate 109a of the blemish 106a approaches closest to the subject coordinate a from among the blemishes whose gravity center positional coordinates exist inside the search range 112 of the second skin image 100. In this case, the matching process unit 17 matches the blemish 106a whose gravity center positional coordinate 109a is closest to the subject coordinate g from among the blemishes having the gravity center positional coordinates inside the search range 112 of the first skin image 100 with the blemish 106g of the second skin image 102 (matching indicated by an arrow of solid line). The matching process unit 17 performs this process for each blemish on the second skin image 102.

Further, in a case where the blemish whose gravity center positional coordinate existing inside the search area of the first skin image 100 is not present, the matching process unit 17 causes an issue that the blemish corresponding to the blemish of the second skin image 102 is not present on the first skin image 100 to be associated with the blemish of the second skin image 102.

The range (the size) of the search range 110 can be within a circle (the radius of the circle is at least 1 pixel) whose actual size is 40 mm around a subject coordinate. Preferably, the range (the size) of the search range 110 can be within a circle having the radius so that the actual size is at least 1 mm and at most 2 mm around the subject coordinate. The actual size means the real size of the subject whose skin image has been captured. For example, a real size of a site such as a cheek.

The range (the size) of the search range 112 can be similar to, for example, the search range 110. As described above, the search ranges are the same in the case where the blemish is searched based on the gravity center positional coordinate of the blemish of the first skin image 100 out of the second skin image 102 and in the case where the blemish is searched based on the gravity center positional coordinate of the blemish of the second skin image 102 out of the first skin image 100. Therefore, matching of the blemishes between the first skin image 100 and the second skin image 102 can be performed without contradiction. Further, split and junction of the blemishes can be detected using the same standard. However, the size of the search range 110 may differ from the size of the search range 112.

The size of the search range may be dynamically determined based on the mean value or the like of the planar dimensions of the blemishes detected in step S104 illustrated in FIG. 3. However, the size of the search range 110 may be the same as and differ from the size of the search range 112.

Figure 8:
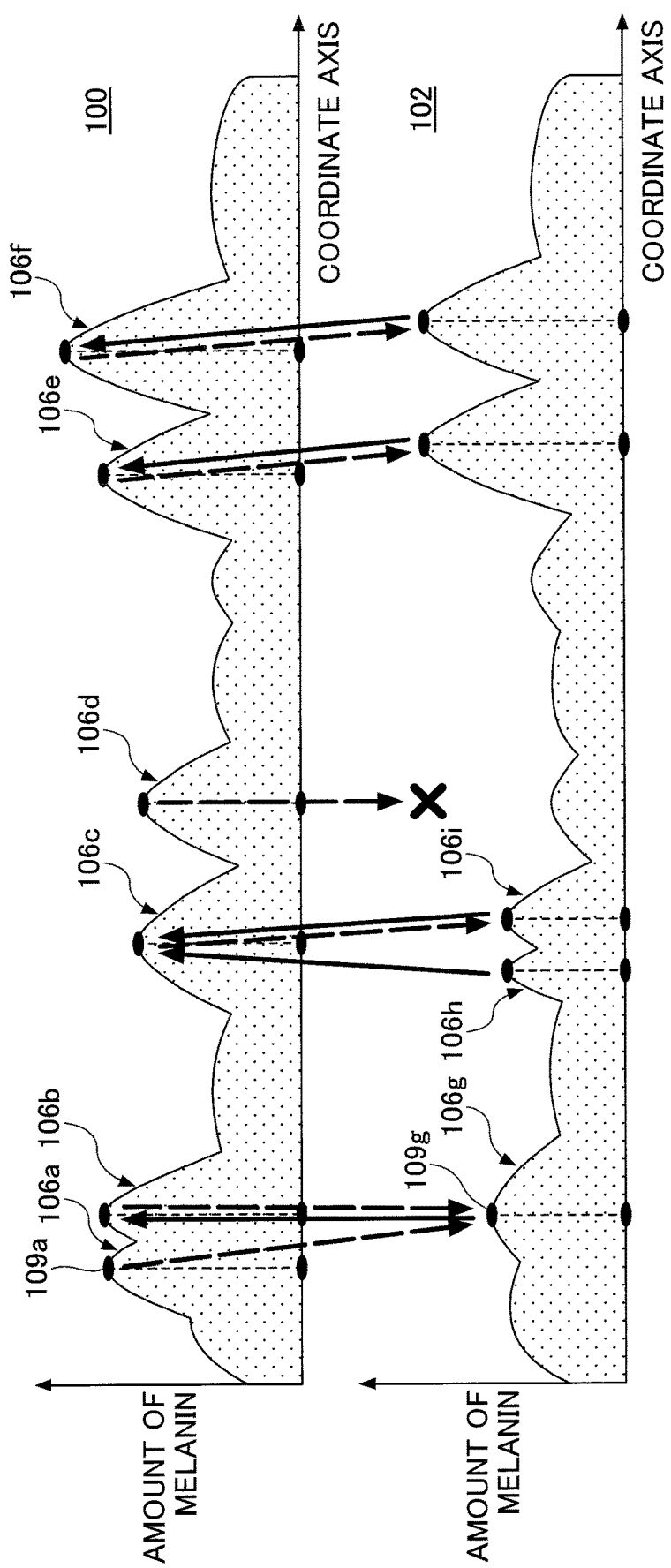
FIG. 8 schematically illustrates an example of matching relation between multiple blemishes in the first skin image and the second skin image in a case where the process illustrated in FIG. 7 is performed.
Figure 9A:
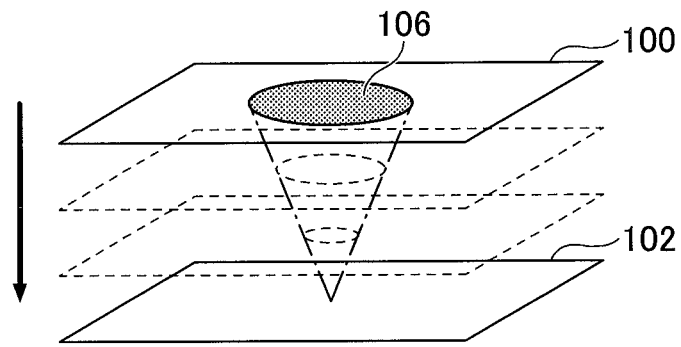
FIG. 9A illustrates a change pattern of the blemish.
Figure 9B:
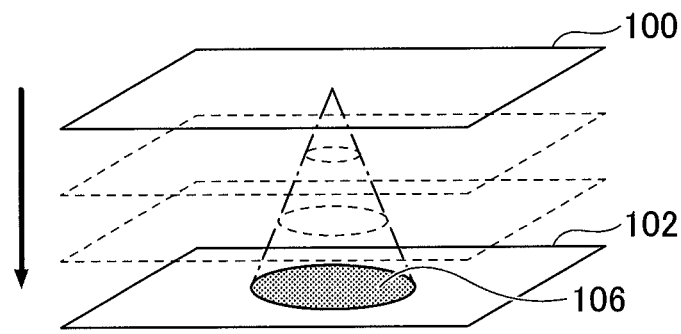
FIG. 9B illustrates another change pattern of the blemish.
Figure 9C:
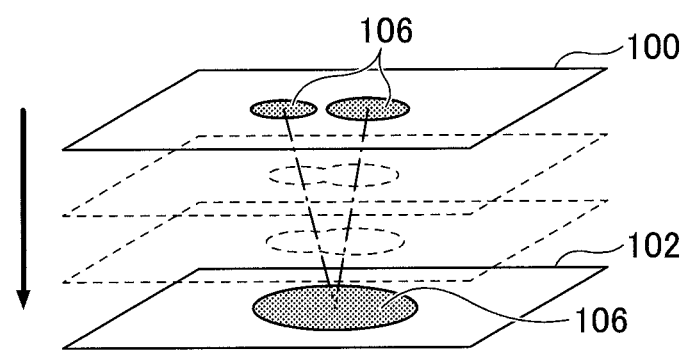
FIG. 9C illustrates another change pattern of the blemish.
Figure 9D:
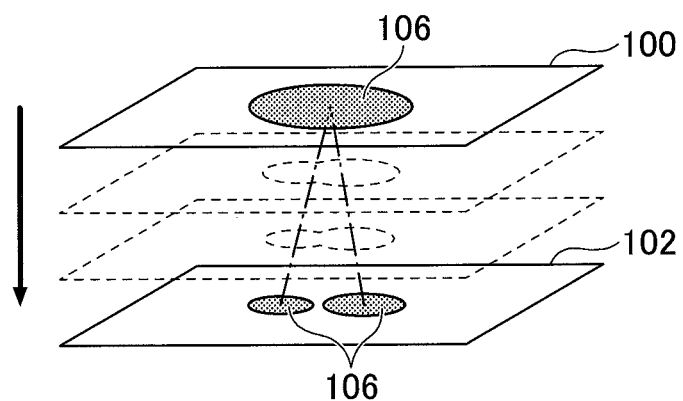
FIG. 9D illustrates another change pattern of the blemish.
Figure 9E:
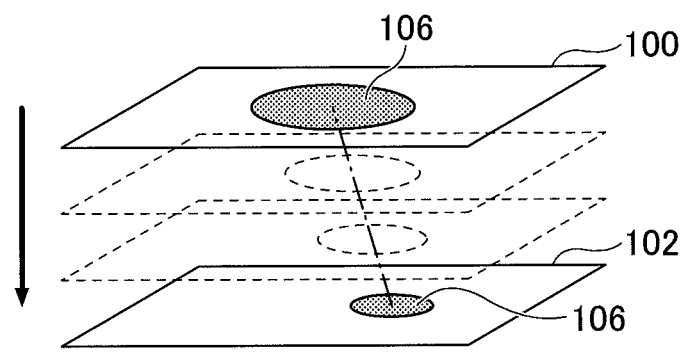
FIG. 9E illustrates another change pattern of the blemish.

FIG. 8 schematically illustrates an example of matching relation between multiple blemishes in the first skin image and the second skin image in a case where the processes described above are performed.

In FIG. 8, (a) corresponds to the first skin image 100, and (b) corresponds to the second skin image 102. In FIG. 8, the arrow of the broken line represents a matching result obtained in the first searching step. In FIG. 8, the arrow of the solid line represents the matching result obtained in the second searching step.

For example, in a case where the second searching step is performed, the blemish 106g of the second skin image 102 is only matched with the blemish 106b of the first skin image 100. Meanwhile, it is possible to know that the blemishes 106a and 106b of the first skin image 100 match the blemish 106g of the second skin image 102 by additionally performing the first searching step. With this, junction of blemishes can be detected.

For example, in a case where the first searching step is performed, the blemish 106c of the first skin image 100 is only matched with the blemish 106i of the second skin image 102 in a manner similar thereto. Meanwhile, it is possible to know that the blemishes 106h and 106i of the second skin image 102 match the blemish 106c of the first skin image 10 by additionally performing the second searching step. With this, split of blemishes can be detected.

For example, by performing the first searching step, it is possible to detect that the blemish corresponding to the blemish 106d of the first skin image 100 is not included in the second skin image 102. With this, disappearance of the blemish can be detected. Although it is not illustrated, by performing the second searching step, it is possible to detect the first skin image 100 without having a blemish corresponding to the blemish included in the second skin image 102. With this, generation of the blemish can be detected.

As described above, it is possible to detect a corresponding relation among the blemishes by performing both the first searching step and second searching step. Whichever of the first searching step and the second searching step can be conducted earlier.

Referring back to FIG. 3, the blemish evaluation unit evaluates the change pattern or the like of the blemish based on the result of the matching step performed by the matching process unit 17. FIGS. 9A to 9E illustrate change patterns of the blemishes.

For example, the blemish evaluation unit 18 evaluates, in the first searching step performed by the matching process unit 17, that the blemish of the first skin image 100 disappears (see FIG. 9A) in a case where there is no blemish whose gravity center positional coordinate is present inside the search area for the second skin image 102 corresponding to the blemish 106 of the first skin image 100.

For example, the blemish evaluation unit 18 evaluates, in the second searching step performed by the matching process unit 17, that the blemish of the second skin image 102 is generated (see FIG. 9B) in a case where there is no blemish whose gravity center positional coordinate is present inside the search area for the first skin image 100 corresponding to the blemish of the second skin image 102.

Further, the blemish evaluation unit 18 evaluates, in the first searching step performed by the matching process unit 17, that the multiple blemishes 106 of the first skin image 100 join (see FIG. 9C) in a case where the multiple blemishes 106 of the first skin image 100 match the single blemish 106 of the second skin image 102.

Further, the blemish evaluation unit 18 evaluates, in the second searching step performed by the matching process unit 17, that the multiple blemishes 106 of the second skin image 102 join (see FIG. 9D) in a case where the multiple blemishes 106 of the second skin image 102 match the single blemish of the first skin image 100.

Further, the blemish evaluation unit 18 evaluates, in the matching process step performed by the matching process unit 17, that the blemish is maintained in a case where the blemish 106 of the first skin image 100 matches the blemish 106 of the second skin image 102 in a one-to-one relation.

Here, rectangulars of broken lines between the first skin image 100 and the second skin image 102 presumably represent transitions between the states of the first skin image 100 and the second skin image 102.

In addition to the detection of the above change pattern, a process of a change in the blemish can be quantitatively analyzed based on changes in the planar dimensions between the matched blemishes, the amounts of melanin, or the like. Further, because the changes in each blemish can be evaluated in spite of evaluation of the entire analyzation area, when a relatively pale blemish is extracted from among multiple blemishes included in the first skin image 100, the change in these blemishes can be selectively analyzed so as to enable examination under various conditions. Therefore, the effect of a medical agent having an effect for a pale blemish can be appropriately evaluated, for example.

FIGS. 10A to 10C illustrate an example of information related to various blemishes obtained by processes of the blemish detection unit 15, the gravity center position calculation unit 16, the matching process unit 17, and the blemish evaluation unit 18. This information is stored in the memory unit 13.

FIGS. 10A and 10B illustrate an example of blemish information related to various blemishes obtained by processes of the blemish detection unit 15, the gravity center position calculation unit 16, the matching process unit 17, and the blemish evaluation unit 18. The blemish information includes items such as a blemish ID, a gravity center position, a planar dimension, the amount of melanin, a blemish classification, and so on. The blemish ID is information specifying each blemish. The gravity center position designates a gravity center positional coordinate of each blemish. The planar dimension designates the planar dimension of each blemish. The amount of melanin designates the amount of melanin of each blemish. The amount of melanin may be the mean value or the like of the amount of melanin of the blemish. The amount of melanin may be stored while matching with each image structuring each blemish. The blemish classification designates the classification of the blemish evaluated by the blemish evaluation unit 18 based on the planar dimension or the amount of melanin of each blemish.

FIG. 100 illustrates an example of blemish matching information indicating a corresponding relation, a change pattern, or the like between the first skin image 100 and the second skin image 102, which are acquired by the processes of the matching process unit 17 and the blemish evaluation unit 18. The blemish correspondence information includes items of the blemish ID of the first skin image 100, the blemish ID of the second skin image 102, a change pattern, a state change, or the like. The change pattern shows a pattern how the blemish included in the first skin image changes on the second skin image 1002. The state change designates a state change such as a change in the planar dimension, a change in the amount of melanin of the blemish. (Example for verifying accuracy)

Described next is a result of verifying the matching process of matching the blemishes by the blemish evaluation apparatus of this embodiment. Here, a predetermined medical agent is applied to a certain test subject for a predetermined time duration, and the blemishes on the first skin image that is acquired before applying the predetermined medical agent and the blemishes on the second skin image that is acquired are matched by using the blemish evaluation apparatus 10. Then, the results of the matching are compared by visual judgement.

As a result, in the step of detecting each blemish included in the first skin image 100 from the second skin image 102 corresponding to the first searching step with reference to FIGS. 3 and 6, 785 pieces from among 791 pieces match the results obtained by the visual judgement where the correct answer rate is 99.2%. Meanwhile, in the step of detecting each blemish included in the second skin image 102 from the first skin image 100 corresponding to the second searching step, 862 pieces from among 868 pieces match the results obtained by the visual judgement where the correct answer rate is 99.3%.

As described above, according to the blemish evaluation apparatus 10 of the present embodiment, it is confirmed that the matching between the first skin image 100 and the second skin image can be highly accurate.

Figure 11A:
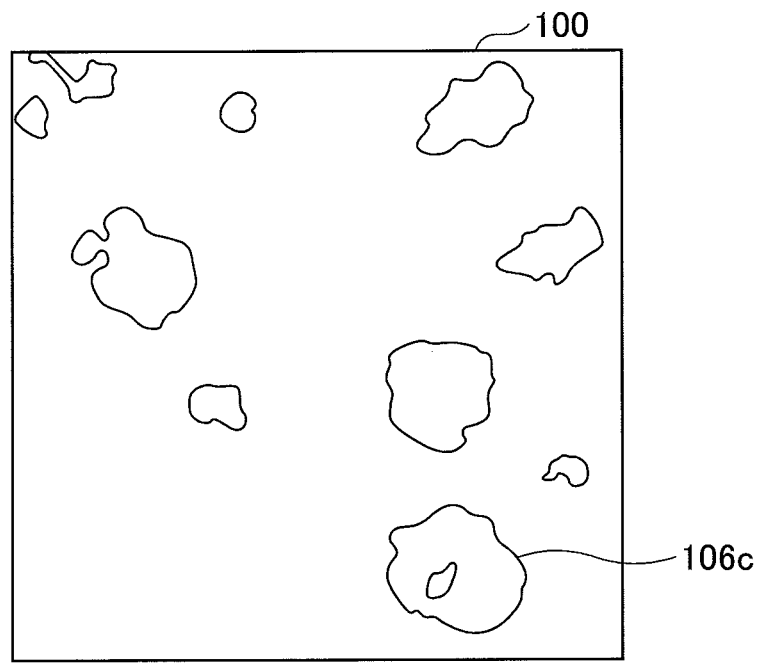
FIG. 11A illustrates a specific example of a blemish matched by a blemish evaluation apparatus of the embodiment.
Figure 11B:
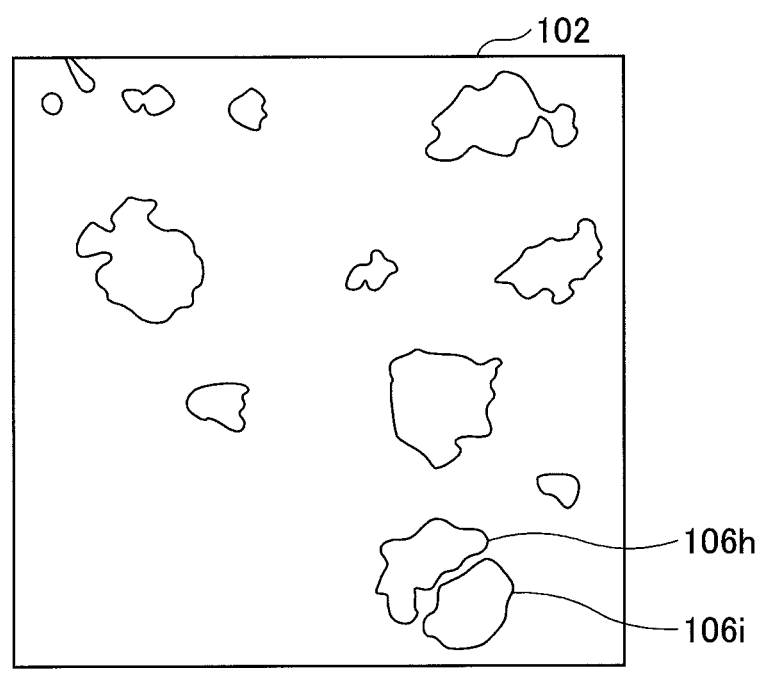
FIG. 11B illustrates a specific example of blemishes matched by the blemish evaluation apparatus of the embodiment.

FIGS. 11A and 11B are parts of the skin image 100 before applying the medical agent and the skin image 102 after applying the medical agent. FIG. 11A illustrates the first skin image 100, and FIG. 11B illustrates the second skin image 102. In the blemish evaluation apparatus 10 of this embodiment, the blemish 106e illustrated in FIG. 11A matches the blemishes 106f and 106g illustrated in FIG. 11B. As described, according to the blemish evaluation apparatus 10 of this embodiment, a change can be known and evaluated for each blemish whose change had not been individually known by the conventional technique.

According to the blemish evaluation process of this embodiment, the change in each blemish included in the skin image can be captured and evaluated. Specifically, by matching the multiple blemishes on the first skin image and the multiple blemishes on the second skin image whose subject portion of the test subject is the same as that of the first skin image and whose captured time is different from that of the first skin image, the change in the each blemish can be known. For example, it is possible to know how a small blemish change, how a large blemish change, how a deep blemish change, and how a pale blemish change.

Further, it is possible to know an effect of the medical agent in more detail based on the change between the blemishes on the images before and after applying a medical agent such as a skin-whitening medical agent for the same test subject. By this, for example, a cosmetic products manufacturer or the like can propose the most suitable product for a customer depending on the condition or the trouble of the skin of the customer. Further, depending on the change of the blemish on aging change images of an identical test subject, a process of generating or worsening the blemish along with the aging can be quantitatively analyzed to create basic understanding.

Although there has been described about the embodiments, the present invention is not limited to the above specific embodiments, and various modifications and changes are possible in a scope of the present invention recited in the claims.

Within the embodiment, although the first skin image 100 and the second skin image 102 are described, the number of the skin images acquired by the image acquiring unit 14 may be or more. In this case, it is possible to detect the corresponding relation between the blemishes on earlier and later skin images in time series.

Meanwhile, the color of skin is determined by adsorption of light by "hemoglobin pigment" and "melanin pigment". The pigment exerting a skin color such as hemoglobin and melanin component is not uniformly distributed inside the skin, and when the pigment is excessively generated at local places, the color tone of the skin surface becomes uneven. This state is generally referred to as color irregularity. In the color irregularity, a symptom whose factor is hemoglobin pigment is "acne", "acne scar", and so on, and a symptom whose factor is melanin pigment is "blemish (senile pigment freckle or solar lentigo, post-inflammatory pigmentation, freckle, chloasma, or the like)", "lentigo", and so on. Within this embodiment, these symptoms are the subject. Within the embodiment, described is the case where the color irregularity site is blemish. However, the color irregularity site as the subject is not limited to blemish and may be various things specified by the pigment composition such as the melanin component and the hemoglobin component or a color level, for example, acne, acne scar, eruption, burn mark, lentigo, or the like. The color irregularity site evaluation process is useful when the subject is the color irregularity site especially causing a time-dependent change.

Further, the blemish evaluation unit 18 may display the first skin image 100 and the second skin image 102 through the output unit 12 on the output device 22 such as a display. At this time, for example, the user of the blemish evaluation apparatus 10 selects the predetermined blemish 106C by a pointer or the like on the first skin image 100, the blemishes 106h and 106i on the second skin image 102 may be impressively displayed. With this, the user can visually confirm how each blemish on the first skin image 100 changes on the second skin image 102.

This international application is based on Japanese Priority Patent Application No. 2016-082380 filed on Apr. 15, 2016, the entire contents of which are hereby incorporated herein by reference.

EXPLANATION OF THE REFERENCE NUMERALS

10: blemish evaluation apparatus
11: input unit
12: output unit
13: memory unit
14: image acquiring unit
15: blemish detection unit
16: gravity center position calculation unit
17: matching process unit
18: blemish evaluation unit
19: control unit
21: input device
22: output device
23: drive device
24: auxiliary storage device
25: memory device
26: CPU
27: network connection device
28: recording medium
100: first skin image
102: second skin image
106: blemish
108: gravity center
110: search range
112: search range

The invention claimed is:

1. An evaluation method of evaluating a color irregularity site comprising:
   a color irregularity site detection step of detecting a plurality of color irregularity sites respectively from a first skin image and a second skin image different from the first skin image;
   a gravity center position calculation step of calculating gravity center positional coordinates of the color irregularity sites respectively for the first skin image and the second skin image; and
   a matching process step of matching the plurality of color irregularity sites included in the first skin image with the plurality of color irregularity sites included in the second skin image based on the calculated gravity center positional coordinates of the color irregularity sites.

2. The evaluation method of evaluating the color irregularity site according to claim 1,
   wherein the first skin image and the second skin image is a skin image obtained by capturing an identical subject portion of an identical test subject at different times.

3. The evaluation method of evaluating the color irregularity site according to claim 1, the evaluation method further comprising:
   a step of performing a position alignment between the first skin image and the second skin image based on multiple color irregularity sites detected from the first skin image and multiple color irregularity sites detected from the second skin image and deteimining a reference point of the coordinate,
   wherein, in the gravity center position calculation step, the gravity center positional coordinate of the color irregularity site with respect to the reference point is calculated.

4. The evaluation method of evaluating the color irregularity site according to claim 1,
   wherein the color irregularity site is a blemish, and
   wherein, in the color irregularity site detection step, the multiple color irregularity sites are detected based on a distribution image of a melanin component or a hemoglobin component.

5. The evaluation method of evaluating the color irregularity site according to claim 1,
   wherein the matching process step includes a first searching step that
      searches the second skin image for each color irregularity site on the first skin image within a predetermined range as a search area around a subject coordinate of the second skin image corresponding to the gravity center positional coordinate,
      causes the color irregularity site whose gravity center positional coordinate approaches closest to the subject coordinate to match the color irregularity site on the first skin image from among the color irregularity site whose gravity center positional coordinate is present inside the search area, and
      causes, in a case where the color irregularity site whose gravity center positional coordinate is present inside the search area is not present, to associate an event in which the color irregularity site corresponding to the color irregularity site on the first skin image is not present on the second skin image with the color irregularity site on the first skin image.

6. The evaluation method of evaluating the color irregularity site according to claim 5,
   wherein the matching process step includes a second searching step that
      searches the first skin image for each color irregularity site on the second skin image within a predetermined range as a search area around a subject coordinate of the first skin image corresponding to the gravity center positional coordinate,
      causes the color irregularity site whose gravity center positional coordinate approaches closest to the subject coordinate to match the color irregularity site on the second skin image from among the color irregularity site whose gravity center positional coordinate is present inside the search area, and
      causes, in a case where the color irregularity site whose gravity center positional coordinate is present inside the search area is not present, to associate an event in which the color irregularity site corresponding to the color irregularity site on the second skin image is not present on the first skin image with the color irregularity site on the second skin image.

7. The evaluation method of evaluating the color irregularity site according to claim 6,
   wherein the second skin image is a skin image obtained by capturing the same subject portion of the same test subject as that of the first skin image at a time later than a time when the first skin image is captured,
   wherein the evaluation method of evaluating the color irregularity site further comprises:
      an evaluation of evaluating a change between the color irregularity site of the first and second skin images based on the matching determined in the matching process step between the multiple color irregularity sites included in the first skin image and the multiple color irregularity sites included in the second skin image.

8. The evaluation method of evaluating the color irregularity site according to claim 7,
wherein, the evaluation step,
in a case where the first searching step of the matching process step does not find the color irregularity site having the gravity center positional coordinate within the search area, determines that the color irregularity site of the first skin image disappears, and
in a case where the second searching step of the matching process step does not find the color irregularity site having the gravity center positional coordinate within the search area, determines that the color irregularity site of the second skin image is generated.

9. The evaluation method of evaluating the color irregularity site according to claim 7,
wherein, the evaluation step,
in a case where the multiple color irregularity sites of the first skin image are determined to match one of the color irregularity sites of the second skin image in the first searching step, evaluates that the multiple color irregularity sites of the first skin image join, and
in a case where the multiple color irregularity sites of the second skin image are determined to match one of the color irregularity sites of the first skin image in the first searching step, evaluates that the color irregularity site of the first skin image split.

10. A color irregularity site evaluation apparatus comprising:
a color irregularity site detection unit configured to detect a plurality of color irregularity sites respectively from a first skin image and a second skin image different from the first skin image;
a gravity center position calculation unit configured to calculate gravity center positional coordinates of the color irregularity sites respectively for the first skin image and the second skin image; and
a matching process unit configured to match the plurality of color irregularity sites included in the first skin image with the plurality of color irregularity sites included in the second skin image based on the calculated gravity center positional coordinates of the color irregularity sites.

11. A non-transitory recording medium storing a color irregularity site evaluating program readable by a computer, the color irregularity site evaluating program causes a computer to function as:
a color irregularity site detection means configured to detect a plurality of color irregularity sites respectively from a first skin image and a second skin image different from the first skin image;
a gravity center position calculation means configured to calculate gravity center positional coordinates of the color irregularity sites respectively for the first skin image and the second skin image; and
a matching process means configured to match the plurality of color irregularity sites included in the first skin image with the plurality of color irregularity sites included in the second skin image based on the calculated gravity center positional coordinates of the color irregularity sites.

\* \* \* \* \*